(12) United States Patent
Snow et al.

(10) Patent No.: US 11,986,321 B2
(45) Date of Patent: May 21, 2024

(54) SYSTEM AND METHOD FOR DETECTING AND REMOVING PERIODIC NON-PHYSIOLOGICAL ARTIFACT FROM EVOKED POTENTIALS

(71) Applicant: SafeOp Surgical, Inc., Hunt Valley, MD (US)

(72) Inventors: Cameron Snow, Phoenix, MD (US); Richard O'Brien, Hunt Valley, MD (US); Gregg Johns, Toronto (CA)

(73) Assignee: Safeop Surgical, Inc., Hunt Valley, MD (US)

( * ) Notice: Subject to any disclaimer, the term of this patent is extended or adjusted under 35 U.S.C. 154(b) by 0 days.

(21) Appl. No.: 15/710,749

(22) Filed: Sep. 20, 2017

(65) Prior Publication Data
US 2018/0078210 A1 Mar. 22, 2018

Related U.S. Application Data

(60) Provisional application No. 62/398,419, filed on Sep. 22, 2016.

(51) Int. Cl.
*A61B 5/00* (2006.01)
*A61B 5/0205* (2006.01)
(Continued)

(52) U.S. Cl.
CPC .......... *A61B 5/7203* (2013.01); *A61B 5/0205* (2013.01); *A61B 5/316* (2021.01);
(Continued)

(58) Field of Classification Search
CPC ...... A61N 1/36014; A61N 1/18; G11B 20/24; A61B 5/7203; A61B 5/0205;
(Continued)

(56) References Cited

U.S. PATENT DOCUMENTS

| 4,161,945 A | 7/1979 | Grossman | |
| 4,291,703 A * | 9/1981 | Kelen | A61B 5/04365 600/524 |

(Continued)

FOREIGN PATENT DOCUMENTS

| CN | 101137332 A | 3/2008 |
| CN | 101309419 A | 11/2008 |

(Continued)

OTHER PUBLICATIONS

"NeuroStream—Intraoperative Monitoring Document Management" [online][retrieved Apr. 21, 2010]. Retrieved from the Internet at <http://www.neurostream.us/solutionsonlineDoc.iso?nav=1>.

(Continued)

*Primary Examiner* — Alyssa M Alter
*Assistant Examiner* — Jessandra F Hough
(74) *Attorney, Agent, or Firm* — Dentons Durham Jones Pinegar; Sarah W. Matthews

(57) ABSTRACT

An automated electrophysiological response analysis apparatus for identifying and eliminating signals having non-physiological artifact noise from an averaged evoked potential signal, wherein the apparatus is adapted to identify in an electrophysiological response at least one characteristic representative of non-physiological artifact noise to classify the signal as an artifact signal and remove the artifact signal from a collection of signals used to generate the averaged evoked potential signal.

7 Claims, 7 Drawing Sheets

(51) Int. Cl.
  *A61B 5/316* (2021.01)
  *A61B 5/377* (2021.01)
  *A61N 1/18* (2006.01)
  *A61N 1/36* (2006.01)
  *G11B 20/24* (2006.01)
  *G16H 40/63* (2018.01)

(52) U.S. Cl.
  CPC ............ *A61B 5/377* (2021.01); *A61B 5/7217* (2013.01); *A61N 1/36014* (2013.01); *G11B 20/24* (2013.01); *G16H 40/63* (2018.01); *A61B 2560/0247* (2013.01); *A61N 1/18* (2013.01)

(58) Field of Classification Search
  CPC . A61B 5/04017; A61B 5/0484; A61B 5/7217; A61B 2560/0247
  See application file for complete search history.

(56) References Cited

U.S. PATENT DOCUMENTS

| | | | |
|---|---|---|---|
| 4,305,402 A | 12/1981 | Katims | |
| 4,863,265 A | 9/1989 | Flower et al. | |
| 4,934,377 A | 6/1990 | Bova et al. | |
| 5,139,028 A * | 8/1992 | Steinhaus | A61B 5/0006 600/508 |
| 5,184,615 A * | 2/1993 | Nappholz | A61N 1/3622 607/14 |
| 5,284,154 A | 2/1994 | Raymond et al. | |
| 5,313,956 A | 5/1994 | Knutsson et al. | |
| 5,662,105 A | 9/1997 | Tien | |
| 5,797,854 A | 8/1998 | Hedgecock | |
| 5,825,936 A | 10/1998 | Clarke et al. | |
| 5,827,195 A | 10/1998 | Lander | |
| 5,916,179 A | 6/1999 | Sharrock | |
| 6,067,467 A * | 5/2000 | John | A61B 5/4821 600/544 |
| 6,304,772 B1 * | 10/2001 | Taha | A61B 5/7203 600/510 |
| 6,391,024 B1 | 5/2002 | Sun et al. | |
| 6,535,767 B1 | 3/2003 | Kronberg | |
| 6,556,861 B1 | 4/2003 | Prichep | |
| 6,634,043 B2 | 10/2003 | Lamb et al. | |
| 6,725,086 B2 | 4/2004 | Marinello | |
| 6,985,833 B2 | 1/2006 | Shambroom et al. | |
| 7,174,206 B2 | 2/2007 | Frei et al. | |
| 7,216,001 B2 | 5/2007 | Hacker et al. | |
| 7,234,180 B2 | 6/2007 | Horton et al. | |
| 7,286,871 B2 * | 10/2007 | Cohen | A61B 5/04004 600/300 |
| 7,512,439 B1 | 3/2009 | Farazi | |
| 7,522,953 B2 | 4/2009 | Kaula et al. | |
| 7,620,453 B1 | 11/2009 | Propato et al. | |
| 7,628,757 B1 | 12/2009 | Koh | |
| 7,628,761 B2 | 12/2009 | Gozani et al. | |
| 7,806,862 B2 | 10/2010 | Molnar | |
| 7,904,160 B2 | 3/2011 | Brodnick et al. | |
| 8,055,349 B2 | 11/2011 | Gharib et al. | |
| 8,108,039 B2 | 1/2012 | Saliga et al. | |
| 8,255,045 B2 | 8/2012 | Gharib et al. | |
| 8,386,025 B2 | 2/2013 | Hoppe | |
| 8,440,903 B1 | 5/2013 | Farris, III | |
| 8,515,530 B2 | 8/2013 | Warner et al. | |
| 8,538,512 B1 | 9/2013 | Bibian et al. | |
| 8,538,539 B2 | 9/2013 | Gharib et al. | |
| 8,568,331 B2 | 10/2013 | Bertagnoli et al. | |
| 8,591,431 B2 | 11/2013 | Calancie et al. | |
| 8,731,654 B2 | 5/2014 | Johnson et al. | |
| 8,740,783 B2 | 6/2014 | Gharib et al. | |
| 8,903,487 B1 | 12/2014 | Fischell et al. | |
| 8,965,520 B2 | 2/2015 | Botros et al. | |
| 8,989,866 B2 | 3/2015 | Gharib et al. | |
| 9,084,551 B2 | 7/2015 | Brunnett et al. | |
| 9,211,074 B2 | 12/2015 | Johnson et al. | |
| 9,332,918 B1 | 5/2016 | Buckley et al. | |
| 9,579,037 B2 | 2/2017 | Brunnett et al. | |
| 9,585,618 B2 | 3/2017 | Leschinsky | |
| 9,681,880 B2 | 6/2017 | Neubardt et al. | |
| 9,700,228 B2 | 7/2017 | Gharib et al. | |
| 9,743,853 B2 | 8/2017 | Kelleher | |
| 9,743,884 B2 | 8/2017 | Rasmussen | |
| 9,744,356 B2 | 8/2017 | Botros et al. | |
| 10,342,443 B2 | 7/2019 | Johnson et al. | |
| 10,376,167 B2 | 8/2019 | Mahon et al. | |
| 10,391,012 B2 | 8/2019 | Stashuk et al. | |
| 11,083,387 B2 | 8/2021 | Mahon et al. | |
| 11,197,640 B2 | 12/2021 | Johns et al. | |
| 11,684,533 B2 | 6/2023 | Stashuk et al. | |
| 2002/0042563 A1 | 4/2002 | Becerra et al. | |
| 2002/0183605 A1 | 12/2002 | Devlin et al. | |
| 2003/0052775 A1 | 3/2003 | Shambroom et al. | |
| 2003/0083719 A1 | 5/2003 | Shankar et al. | |
| 2003/0125777 A1 * | 7/2003 | Ding | A61N 1/3712 607/27 |
| 2003/0176799 A1 | 9/2003 | Beatty et al. | |
| 2004/0010303 A1 | 1/2004 | Bolea | |
| 2004/0122482 A1 | 6/2004 | Tung et al. | |
| 2005/0075578 A1 | 4/2005 | Gharib et al. | |
| 2005/0085866 A1 | 4/2005 | Tehrani | |
| 2005/0101878 A1 | 5/2005 | Daly et al. | |
| 2005/0119711 A1 | 6/2005 | Cho et al. | |
| 2005/0228306 A1 | 10/2005 | Kurtz | |
| 2005/0228654 A1 | 10/2005 | Prieto et al. | |
| 2005/0261559 A1 | 11/2005 | Mumford et al. | |
| 2006/0025702 A1 | 2/2006 | Sterrantino et al. | |
| 2006/0052845 A1 | 3/2006 | Zanella | |
| 2006/0173510 A1 | 8/2006 | Besio et al. | |
| 2006/0178593 A1 | 8/2006 | Neubardt et al. | |
| 2006/0241562 A1 | 10/2006 | John et al. | |
| 2006/0276704 A1 | 12/2006 | McGinnis et al. | |
| 2007/0016097 A1 | 1/2007 | Farquhar et al. | |
| 2007/0135722 A1 | 6/2007 | Lin | |
| 2007/0192960 A1 | 8/2007 | Jackson | |
| 2007/0225674 A1 | 9/2007 | Molnar et al. | |
| 2007/0282217 A1 | 12/2007 | McGinnis et al. | |
| 2008/0033511 A1 | 2/2008 | Dobak | |
| 2008/0051844 A1 | 2/2008 | Brodnick et al. | |
| 2008/0167574 A1 | 7/2008 | Farquhar | |
| 2008/0221473 A1 | 9/2008 | Calancie et al. | |
| 2008/0269835 A1 | 10/2008 | Carlson et al. | |
| 2008/0300655 A1 | 12/2008 | Cholette | |
| 2009/0033486 A1 | 2/2009 | Costantino | |
| 2009/0048531 A1 | 2/2009 | McGinnis et al. | |
| 2009/0054758 A1 | 2/2009 | Dunseath | |
| 2009/0054804 A1 | 2/2009 | Gharib et al. | |
| 2009/0069027 A1 | 3/2009 | Brock et al. | |
| 2009/0124869 A1 | 5/2009 | Hu et al. | |
| 2009/0143693 A1 | 6/2009 | Ye et al. | |
| 2009/0177112 A1 | 7/2009 | Gharib et al. | |
| 2009/0247893 A1 | 10/2009 | Lapinlampi et al. | |
| 2010/0010367 A1 | 1/2010 | Foley et al. | |
| 2010/0036211 A1 | 2/2010 | La Rue et al. | |
| 2010/0042012 A1 | 2/2010 | Alhussiny | |
| 2010/0130834 A1 | 5/2010 | Viertio-Oja et al. | |
| 2010/0156376 A1 | 6/2010 | Fu et al. | |
| 2010/0198099 A1 | 8/2010 | Murphy et al. | |
| 2010/0274144 A1 | 10/2010 | Hu et al. | |
| 2010/0312124 A1 * | 12/2010 | Johnson | A61B 5/04001 600/485 |
| 2010/0317989 A1 | 12/2010 | Gharib et al. | |
| 2011/0054346 A1 | 3/2011 | Hausman et al. | |
| 2011/0224570 A1 | 9/2011 | Causevic | |
| 2011/0224988 A1 | 9/2011 | Mahajan et al. | |
| 2011/0230785 A1 | 9/2011 | Higgins et al. | |
| 2011/0279676 A1 | 11/2011 | Terada et al. | |
| 2011/0295142 A1 | 12/2011 | Chakravarthy et al. | |
| 2012/0065536 A1 | 3/2012 | Causevic et al. | |
| 2012/0095360 A1 | 4/2012 | Runney et al. | |
| 2012/0136276 A1 | 5/2012 | Johnson et al. | |
| 2012/0150063 A1 | 6/2012 | Rea | |
| 2012/0165690 A1 | 6/2012 | Chen et al. | |
| 2012/0197153 A1 | 8/2012 | Kraus et al. | |
| 2012/0313757 A1 | 12/2012 | Volpi et al. | |
| 2013/0024524 A1 | 1/2013 | Graff et al. | |

(56) References Cited

U.S. PATENT DOCUMENTS

| | | | |
|---|---|---|---|
| 2013/0035606 A1 | 2/2013 | Wichner | |
| 2013/0138356 A1* | 5/2013 | Nierenberg | A61B 5/4552 702/19 |
| 2013/0190599 A1 | 7/2013 | Wyeth et al. | |
| 2013/0204156 A1 | 8/2013 | Hampton et al. | |
| 2013/0245424 A1 | 9/2013 | Decharms | |
| 2013/0245722 A1 | 9/2013 | Ternes et al. | |
| 2014/0020178 A1 | 1/2014 | Stashuk et al. | |
| 2014/0121555 A1 | 5/2014 | Scott et al. | |
| 2014/0148725 A1 | 5/2014 | Cadwell | |
| 2014/0275926 A1 | 9/2014 | Scott | |
| 2014/0276195 A1 | 9/2014 | Papay et al. | |
| 2014/0288389 A1 | 9/2014 | Gharib et al. | |
| 2014/0324118 A1 | 10/2014 | Simon et al. | |
| 2015/0061758 A1 | 3/2015 | Hsu | |
| 2015/0088030 A1 | 3/2015 | Taylor | |
| 2015/0148683 A1 | 5/2015 | Hermanne | |
| 2015/0208934 A1 | 7/2015 | Sztrubel et al. | |
| 2015/0257700 A1 | 9/2015 | Fu | |
| 2015/0305640 A1* | 10/2015 | Reinke | A61B 5/316 600/510 |
| 2015/0313512 A1 | 11/2015 | Hausman et al. | |
| 2016/0106994 A1 | 4/2016 | Crosby et al. | |
| 2016/0113587 A1 | 4/2016 | Kothe et al. | |
| 2016/0128620 A1 | 5/2016 | Iriki et al. | |
| 2016/0213268 A1 | 7/2016 | Kim et al. | |
| 2016/0228018 A1 | 8/2016 | Mahon et al. | |
| 2016/0270679 A1 | 9/2016 | Mahon et al. | |
| 2017/0347955 A1 | 12/2017 | Rasmussen | |
| 2018/0078210 A1 | 3/2018 | Snow et al. | |
| 2018/0140843 A1 | 5/2018 | Kent et al. | |
| 2018/0310849 A1 | 11/2018 | Johns et al. | |
| 2018/0360336 A1 | 12/2018 | O'Brien et al. | |
| 2020/0315478 A1 | 10/2020 | Mahon et al. | |
| 2022/0096022 A1 | 3/2022 | Johns et al. | |
| 2022/0287619 A1 | 9/2022 | Cleveland et al. | |

FOREIGN PATENT DOCUMENTS

| | | |
|---|---|---|
| CN | 201185940 Y | 1/2009 |
| CN | 102361590 A | 2/2012 |
| CN | 102368951 A | 3/2012 |
| CN | 102481107 A | 5/2012 |
| CN | 102594472 A | 7/2012 |
| CN | 102824170 A | 12/2012 |
| CN | 102883775 A | 1/2013 |
| CN | 104411234 A | 3/2015 |
| JP | S51154986 U | 12/1976 |
| JP | S5922106 A | 7/1982 |
| JP | S59193403 A | 4/1983 |
| JP | H04253843 A | 12/1991 |
| JP | H06508288 A | 9/1994 |
| JP | H06277189 A | 10/1994 |
| JP | H1176185 A | 3/1999 |
| JP | 2003131668 A | 5/2003 |
| JP | 2004517669 A | 6/2004 |
| JP | 2005073223 A | 3/2005 |
| JP | 2007185326 A | 7/2007 |
| JP | 2009-502424 A | 1/2009 |
| JP | 2009011896 A | 1/2009 |
| JP | 2005519646 A | 4/2009 |
| JP | 2009071387 A | 4/2009 |
| JP | 2009118969 A | 6/2009 |
| JP | 2009534159 A | 9/2009 |
| JP | 2010104586 A | 5/2010 |
| JP | 2012529344 A | 11/2012 |
| JP | 2012236007 A | 12/2012 |
| JP | 5466389 B2 | 4/2014 |
| JP | 2017-502711 A | 1/2017 |
| WO | 2001074248 A1 | 10/2001 |
| WO | 2003000128 A2 | 1/2003 |
| WO | 2003005887 A2 | 1/2003 |
| WO | 2006072050 A2 | 7/2006 |
| WO | 2006084193 A2 | 8/2006 |
| WO | 2010144200 A1 | 12/2010 |
| WO | 2011045936 A1 | 4/2011 |
| WO | 2013166157 A1 | 11/2013 |
| WO | 2015048822 A1 | 5/2015 |
| WO | 2016179191 A1 | 11/2016 |
| WO | 2018232365 A1 | 12/2018 |
| WO | 2022192569 A1 | 9/2022 |

OTHER PUBLICATIONS

"NeuroStream—Intraoperative Monitoring Interpreting Physician Access" [online][retrieved Apr. 21, 2010). Retrieved from the Internet at HYPERLINK "http://www.neurostream.us/solutionstelemedicine.iso?nav=1".

"NeuroStream—IOM and Neurophysiological Monitoring Software" [online][retrieved Apr. 21, 2010). Retrieved from the Internet at HYPERLINK "http://www.neurostream.us/solutionscaseExecution.iso?nav=1".

"NeuroStream—Software for Intraoperative Monitoring Scheduling" [online][retrieved Apr. 21, 2010). Retrieved from the Internet at HYPERLINK h http://www.neurostream.us/solutionsschedulina.iso?nav= 1.

AMSCO 3085 SP Surgical Table Sales Brochure, STERIS Corporation; Apr. 2006, 16 pages.

Baumann, et al., Intraoperative SSEP Detection of Ulnar Nerve Compression or Ischemia in an Obese Patient: A Unique Complication Associated With a Specialized Spinal Retraction System; Archives of Physical Medicine and Rehabilitation, vol. 81.

Ben-David, et al., Prognosis of Intraoperative Brachial Plexus Injury: A Review of 22 cases, British Journal of Anaesthesia, vol. 79, No. 4, Oct. 1997, pp. 440-445.

Bizzarri, et al., Iatrogenic Injury to the Long Thoracic Nerve: An Underestimated Cause of Morbidity After Cardiac Surgery, Texas Heart Institute Journal, vol. 28, No. 4, Jan. 2001,pp. 315-317.

Chung, Induk, et al., "Upper-limb somatosensory evoked potential monitoring in lumbosacral spine surgery: a prognostic marker for position-related ulnar nerve injury." The Spine Journal 9.4 (Apr. 2009): 287-295.

Crum, et al. "Peripheral nerve stimulation and monitoring during operative procedures." Muscles & nerve 35.2: 159-170. (Year: 2007).

Crum, et al. "intraoperative peripheral nerve stimulation and recording." Handbook of Clinical Neurophysiology 8: 364-370. (Year: 2008).

Doemges, et al., "Changes in the Stretch Reflex of the Human First Dorsal Interosseous Muscle During Different Tasks," Journal of Physiology, 1992, pp. 563-573, vol. 447.

European Patent Office acting as International Searching Authority, "Search Report and Written Opinion," International Application No. PCT/US2022/019798, dated Jul. 6, 2022.

European Patent Office, "Extended European Search Report," European Application No. 23188630.0, dated Sep. 5, 2023.

Fishel, et al., Case Report: Postoperative Injuries of Upper Limb Nerves, The Clinical Journal of Pain, vol. 6, No. 2, Jun. 1990, pp. 128-130.

Graham, et al., Brachial Plexus Injury After Median Sternotomy, Journal of Neurology, Neurosurgery, and Psychiatry, vol. 44, Jul. 1981, pp. 621-625.

Hickey et al., "Intraoperative Somatosensory Evoked Potential Monitoring Predicts Peripheral Nerve Injury During Cardiac Surgery", Anesthesiology 78(1), 29-35 (1993).

Hongxuan Zhang et al., "Intraoperative Neurological Monitoring," vol. 25, No. 4, Jul. 1, 2006 (Jul. 1, 2006), pp. 39-45.

International Search Report and Written Opinion for Application No. PCT/US2014/064433, dated Apr. 4, 2015, 10 pages.

International Search Report and Written Opinion for PCT Application No. PCT/US2010/034076, dated Jul. 9, 2010, 8 pages.

International Search Report and Written Opinion, PCT/US16/30605, dated Aug. 8, 2016.

Jellish, et al., Hands-Up Positioning During Asymmetric Sternal Retraction for Internal Mammary Artery Harvest: A Possible Method

(56) References Cited

OTHER PUBLICATIONS to Reduce Brachial Plexus Injury, Anesthesia and Analgesia, vol. 84, No. 2, Feb. 1997, pp. 260-265.
Kamel et al., "The Use of Sematosensory Evoked Potentials to Determine the Relationship Between Patient Positioning and Impending Upper Extremity Nerve Injury During Spine Surgery: A Retrospective Analysis", Anesth Analg 102(5), 1538-1542 (2006).
Labrom et al., "Clinical Usefulness of Somatosensory Evoked Potentials for Detection of Brachial Plexopathy Secondary to Malpositioning in Scoliosis Surgery", Spine 30(18), 2089-2093 (2005).
Makarov, et al., Intraoperative SSEP Monitoring During External Fixation Procedures in the Lower Extremities, Journal of Pediatric Orthopaedics, vol. 16, No. 2, Mar./Apr. 1996, pp. 155-160.
Makarov, et al., Monitoring Peripheral Nerve Function During External Fixation of Upper Extremities, Journal of Pediatric Orthopaedics, vol. 17, No. 5, Sep./Oct. 1997, pp. 663-667.
Makeig, et al., Mining event-related brain dynamics, Trends in Cognitive Sciences. vol. 8, No. 5, May 2004, pp. 204-210.
Nagda, et al., Neer Award 2005: Peripheral Nerve Function During Shoulder Arthoplasty Using Intraoperative Nerve Monitoring, Journal of Shoulder and Elbow Surgery, vol. 16, No. 3, Supplement, May-Jun. 2007, 7 pages.
Posta, Jr., et al., Neurologic Injury in the Upper Extremity After Total Hip Arthroplasty, Clinical Orthopaedics and Related Research, vol. 345, Dec. 1997, pp. 181-186.
Prielipp, et al., Ulnar Nerve Pressure: Influence of Arm Position and Relationship to Somatosensory Evoked Potentials, Anesthesiology, vol. 91, No. 2, Aug. 1999, 10 pages.
Supplemental Partial European Search Report for Application No. EP 14 86 1025, dated Jun. 16, 2017.
The International Bureau of WIPO, "International Preliminary Report on Patentability," International Application No. PCT/US2022/019798, dated Sep. 21, 2023.
Warner et al. (Dec. 1994) "Ulnar Neuropathy. Incidence, Outcome, and Risk Factors in Sedated or Anesthetized Patients", Anesthesiology, 81(6):1332-1340.
Winfree, et al., Intraoperative Positioning Nerve Injuries, Surgical Neurology, vol. 63, No. 1, Jan. 2005, pp. 5-18.
European Patent Office, "Communication pursuant to Article 94(3) EPC," European Application No. 18771706.1, dated Jul. 14, 2023.
Japan Patent Office, "Office Action," Japanese Application No. 2022191709, dated Nov. 14, 2023.
International Search Authority, "Search Report and Written Opinion," International Application No. PCT/US/2023/029024, Dec. 15, 2023.
China National Intellectual Property Adminsitration, "Office Action," Chinese Application No. 202110429148.7, Nov. 23, 2023.

* cited by examiner

| Variable | Value | Description |
|---|---|---|
| Slope Threshold | 15 | Minimum rate of change required to alert the algorithm. |
| Window Length (ms) | 2.0 | If a large positive and large negative slope are found within this window, the algorithm continues processing. |
| Amplitude Threshold (μV) | 30 | If the amplitude of a non-physiological signal is larger than this threshold, the algorithm continues processing. |
| Rise Time (ms) | 0.5 | Maximum time required for a non-physiological signal to reach its peak. |
| Activity Threshold (data points) | 3 | Threshold to compare instances of variability between data points. |

Figure 5

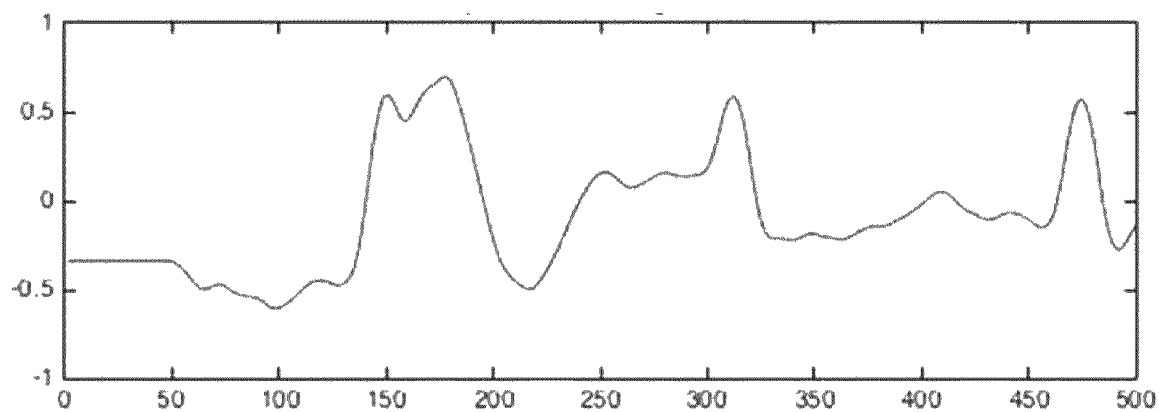

Figure 6A

SYSTEM AND METHOD FOR DETECTING AND REMOVING PERIODIC NON-PHYSIOLOGICAL ARTIFACT FROM EVOKED POTENTIALS

BACKGROUND

The present invention relates generally to the field of removing noise from recorded waveform signals, such as evoked potentials (EPs), and more particularly to a system, method, and computer algorithm for automatically detecting periodic non-physiological artifact and removing if from the EPs.

Bio-electrical potentials such as somatosensory evoked potentials (ssep) are summated electrical potentials usually recorded after stimulating a peripheral nerve or parts of the nervous system. Monitoring patients by recording waveforms such as somatosensory evoked potentials during surgery has been shown to allow early identification of impending nerve injury. The difficulty with analyzing and classifying the waveforms lies in the wide variation in the amplitude, frequency and shape of the waveforms. These variations are caused by many factors including anesthesia and any preexisting abnormalities of the nerves, however one primary cause is electrical interference from ambient electrical noise or from other devices, such as pacemakers.

External pacemakers are an essential part to some cardiac surgeries. Generally, a transcutaneous pacing system is introduced when the patient starts to experience bradycardia (abnormally slow heart action), or if they develop any other irregularities in their heartbeat. Some patients may have internal pacemakers already in place for similar issues. Unfortunately, the electric signals produced by pacing systems are large relative to the ssep being recorded, but often smaller than can be reliably captured by a voltage threshold rejection classifier and contain frequencies not typically excluded by traditional high-pass and low-pass filters used to condition the ssep signals. The electrical interference from the pacing system therefore can represent significant power in the recorded waveforms.

Embodiments herein generally relate to improved systems and methods to automatically and more fully remove pacemaker or similar artifact from recorded ssep signals. The systems and methods overcome many drawbacks caused by non-physiologic, such as pacemaker, noise and drawbacks of current attempts to eliminate such noise. For example, described herein according to some embodiments are systems, methods, and computer signal processing algorithms for the removal of these types of periodic artifacts from evoked potential signals, which can be performed quickly and in real-time without significant processing overhead and without significantly altering the characteristics of the signal of interest.

SUMMARY OF THE INVENTION

One embodiment of the invention relates to an automated EP analysis apparatus for identifying and eliminating signals having non-physiological artifact noise from an averaged EP signal, wherein the apparatus is adapted to identify in an electrophysiological response at least one characteristic representative of non-physiological artifact noise to classify the signal as an artifact signal and remove the artifact signal from a collection of signals used to generate the averaged EP signal.

In some embodiments, the non-physiological artifact noise is pacing artifact from a pacemaker. In some embodiments, the at least one characteristic is at least one from the group consisting of: a minimum slope, minimum amplitude, a maximum rise time, a maximum fall time, a minimum peak duration, and a maximum activity between a rising edge and a falling edge of the signal.

In some embodiments, the apparatus further comprises: an output operable to couple to at least one stimulating electrode to stimulate one or more peripheral nerves of a patient, an input operable to couple to at least one recording electrode to record the electrophysiological response comprising the resultant electrical waveforms generated by a nervous system in response to the one or more stimulating electrodes, and at least one processor, coupled to said output and said input, operable to cause the apparatus to identify in the electrophysiological response at least one characteristic representative of non-physiological artifact noise to classify the signal as an artifact signal and remove the artifact signal from a collection of signals used to generate the averaged EP signal.

Another embodiment of the invention relates to a method for identifying and eliminating signals having non-physiological artifact noise from an averaged EP signal. The method includes recording resultant waveforms generated by a nervous system, resulting from stimulation of one or more nerves of the nervous system, identifying in the resultant waveforms at least one characteristic representative of non-physiological artifact noise, if the at least one characteristic is present in a resultant waveform, classifying the waveform as an artifact signal, and generating an averaged EP signal using only the resultant waveforms that have not been classified as an artifact signal.

In some embodiments, generating an averaged EP signal using only the resultant waveforms that have not been classified as an artifact signal is achieved by removing the artifact signal from a collection of signals used to generate the averaged EP signal. In some embodiments, the non-physiological artifact noise is pacing artifact from a pacemaker. In some embodiments, the at least one characteristic is at least one from the group consisting of: a minimum slope, minimum amplitude, a maximum rise time, a maximum fall time, a minimum peak duration, and a maximum activity between a rising edge and a falling edge of the signal.

In some embodiments, the method further includes identifying a plurality of characteristics representative of non-physiological artifact noise by analyzing the signal for a first characteristic and if the first characteristic is present, continuing to analyze the signal for a second characteristic.

Another embodiment of the invention relates to an automated Evoked Potential (EP) analysis algorithm for monitoring, detecting, identifying and eliminating non-physiological artifact noise in the physiological system from which the EPs or Ensemble Averages (EA) are obtained, wherein the algorithm identifies artifacts in the individual electrophysiological responses (ER) to repetitive stimulation allowing rejection of those containing such artifacts from the ensemble average.

In some embodiments, the non-physiological artifact noise is noise from a pacemaker.

In some embodiments, there is an apparatus for monitoring, detecting, identifying and eliminating non-physiological artifact noise in the physiological system from which the EPs or Ensemble Averages (EA) are obtained, that implements the algorithm described above.

In some embodiments, the apparatus further comprises a system that processes ER sequentially looking for a series of characteristics. In some embodiments, the apparatus further comprises a system that processes ER sequentially looking for a single primary characteristic. In some embodiments, the apparatus further comprises a system that iteratively processes ER meeting a preceding identified characteristic for a further characteristic and stops processing if a characteristic is not found, and rejects a ER from an ensemble average if all characteristics are found.

In some embodiments, the apparatus further comprises a system in which the characteristics comprise but are not limited to amplitude, rise time, fall time, peak duration and pre and post peak slope. In some embodiments, the apparatus further comprises a system in which the characteristics can be altered. In some embodiments, the apparatus further comprises a system in which integrate such apparatus into other devices in a surgical environment. In some embodiments, the apparatus can feed information to other devices in the surgical environment that allows these devices to identify the presence of pacer activity. In some embodiments, the apparatus can obtain information from an anesthesia or blood pressure machine or pacemaker to calculate when changes in EP waveforms are due to anesthesia or physiologic or non-physiologic changes.

BRIEF DESCRIPTION OF THE DRAWINGS

FIG. 5 is a table of threshold values for identifying characteristics of an artifact signal, according to one embodiment.

FIG. 6A depicts an averaged somatosensory evoked potential recording contaminated by pacemaker artifact.

DETAILED DESCRIPTION

Bio-electrical potentials such as somatosensory evoked potentials (ssep) are summated electrical potentials usually recorded after repeatedly stimulating a peripheral nerve or parts of the nervous system. Monitoring patients by recording waveforms such as somatosensory evoked potentials during surgery has been shown to allow early identification of impending nerve injury. Such monitoring is performed with sophisticated, multichannel amplifier and display equipment. This monitoring is often fraught with difficulties due to the small size of potentials and large amounts of ongoing noise which makes recognizing significant changes and when to alert for these changes difficult.

The difficulty with analyzing and classifying the waveforms lies in the wide variation in the amplitude, frequency and shape of the waveforms. These variations are caused by many factors including anesthesia and any preexisting abnormalities of the nerves, however the main cause is electrical interference from ambient electrical noise or from other devices such as pacemakers.

External pacemakers are an essential part to some cardiac surgeries. Generally, a transcutaneous pacing system is introduced when the patient starts to experience bradycardia (abnormally slow heart action), or if they develop any other irregularities in their heartbeat. The anesthesiologist may first attempt to remedy the patient with a drug, but if that fails, pacing is introduced in order to regulate the heartbeat. By providing timed pulses while also recording the hearts activity, the pacing system can bring the patient's heart back into a consistent and natural rhythm. Without the external pacing system, the patient would be more likely to go into cardiac arrest. Other patients may have internal pacemakers in place for similar issues.

Figure 1A:
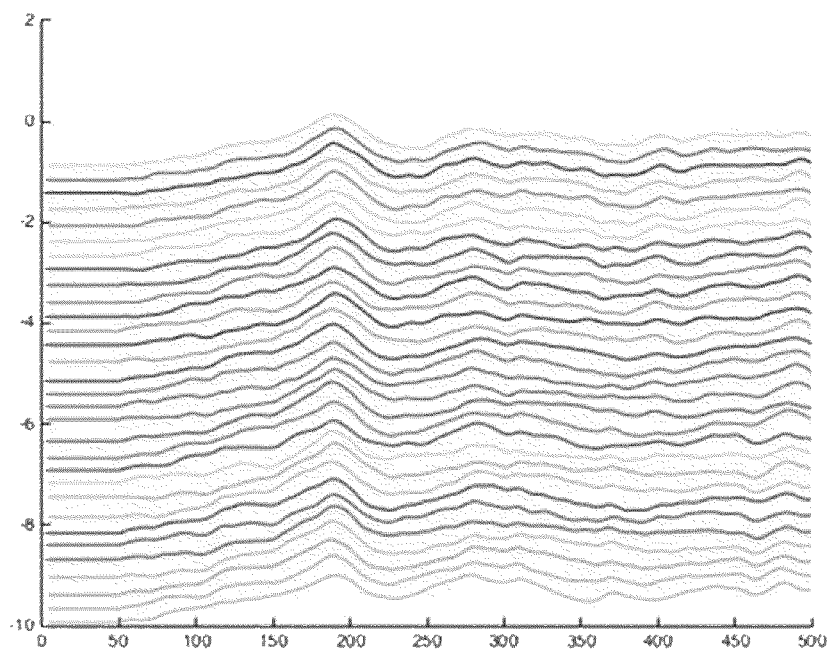
FIG. 1A depicts several evoked potential signals before a pacing signal was applied.
Figure 1B:
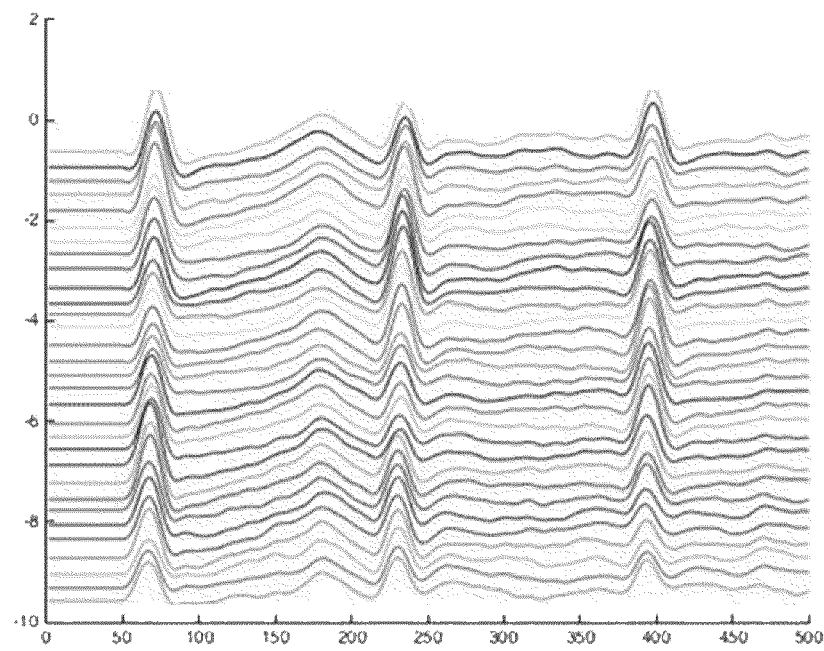
FIG. 1B depicts the evoked potential signals after a pacing signal was applied, showing the effect of the pacing signal on the recorded waveforms.
Figure 2A:
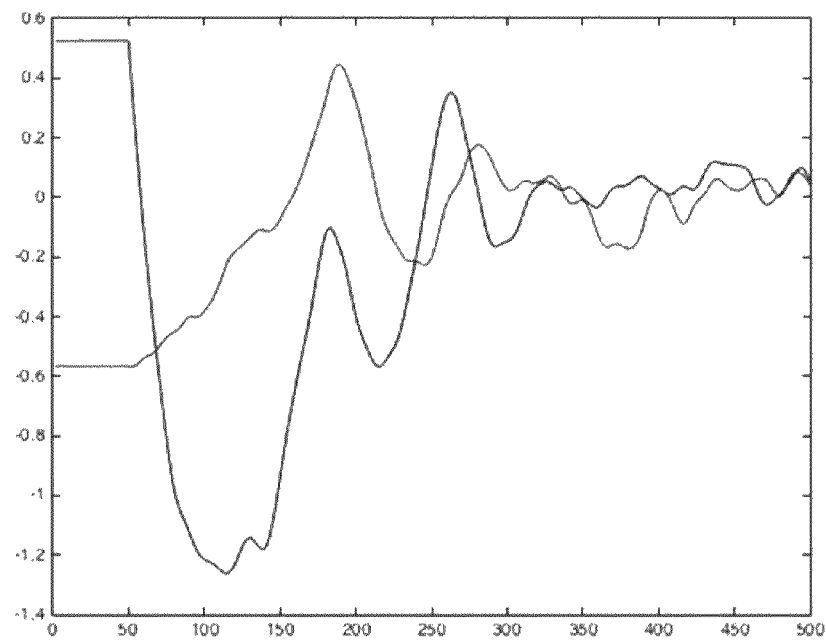
FIG. 2A depicts an averaged signal compared with a baseline signal prior to a pacing signal being applied.
Figure 2B:
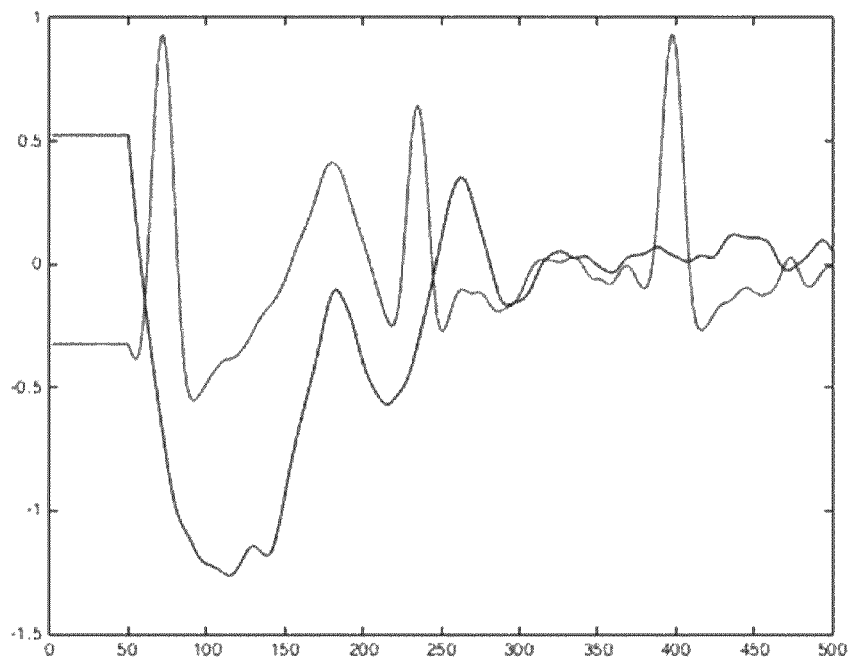
FIG. 2B depicts an averaged signal compared with the baseline when an external pacing signal being applied.

Unfortunately, the electric signals produced by pacing systems are large relative to the somatosensory evoked potential signals being recorded, but often smaller than can be reliably captured by a fixed threshold rejection classifier and contain frequencies not typically attenuated by high- and low-pass filters used to condition the sseps. These electrical signals from the pacing system therefore end up being a major source of noise in the recorded waveforms, as shown in FIGS. 1 and 2. FIG. 1A depicts several signals before a pacing signal was applied, and FIG. 1B depicts the obtained signals after a pacing signal was applied, showing the effect of the pacing signal on the recorded waveforms. Similarly, FIG. 2A depicts an averaged signal compared with a baseline signal prior to a pacing signal being applied, and FIG. 2B depicts an averaged signal compared with the baseline with an external pacing signal being applied. It can be observed how an external pacing signal effects the physiological signals obtained.

Although electronic and digital filters are employed to attenuate noise from the signals and allow better viewing and interpretation of the waveforms, these filters typically filter in two ways, by limiting recoded waveform frequency range or rejecting signals of high amplitude that contain clear artifact, waveform frequency or alteration of the overall data such that only partial removal of noise occurs or the morphology, amplitude or even presence/absence of the underlying potentials that he user is interested in are changed making interpretation difficult and highly dependent on experience. This in turn may lead to erroneous interpretations.

Standard high- and low-pass filters that limit the bandwidth of the recordings, or classifiers that reject raw recordings over a certain amplitude threshold (rejection threshold classifier) may have difficulty removing pacemaker or pacemaker like artifacts from evoked potential recordings, leading to inability to record accurate signals.

There are described methods for detecting and removing pacemaker artifact from electroencephalographic signals, however these primarily apply to continuous EEG or ECG recordings and not to stimulus evoked monitoring. These methods are also complex and introduce significant processor overhead U.S. Pat. No. 8,440,903 (Donehoo) describes a variable amplitude threshold that identifies and eliminates a pacemaker's pulse from data. Once the initial threshold is surpassed by a pacing artifact, the threshold decays in magnitude so that any of the characteristic "ringing" is cut out. However, evoked potentials are not affected by the ringing created by the pacing pulses, and therefore do not have a major need for a variable threshold classifier which adds complexity and additional processing.

Accordingly, certain embodiments disclosed herein provide a lean and fast computer algorithm running on software installed on an evoked potential monitoring machine, which can be used in any surgery or situation where a patient is at risk, to detect and remove confounding pacemaker or similar noise and display the underlying signals more accurately to the user(s).

In an exemplary embodiment of the present invention a system, method, and computer algorithm for identification and removal of pacemaker and pacemaker-like artifact from electrophysiological EPs is disclosed. In this application, an EP is defined as a voltage versus time signal obtained by ensemble averaging (EA) the electrophysiological responses (ER) to repetitive stimulation of a specific sensory neural system detected using suitable electrodes. Examples of EPs are somatosensory, auditory or visual EPs. Ensemble averaging of the electrophysiological responses may be performed according to the system and methods described in U.S. Patent Publication 2014/0020178 entitled "System, Method, and Computer Algorithm and Characterization and Classification of Electrophysiological Evoked Potentials," which is herein incorporated by reference in its entirety.

The methods and algorithms are applied to every ER signal recoded after each stimulation that survives any initial frequency and amplitude rejection filtering, and prior to summation of those timed signals into a EA. The algorithm establishes the presence or absence of a pacemaker or similar artifact in each ER, and then excludes those in which it is present from the EA.

In an exemplary embodiment of the present invention, in order to perform this task with higher efficiency, the algorithm processes the individual signals sequentially in a gated fashion looking for the presence or absence of several characteristics and only performing further examination for remaining characteristics if the preceding characteristic is present. If all characteristics are present, indicative of noise from a pacing or other similar pulse, it rejects the ER from the EA.

Figure 3:
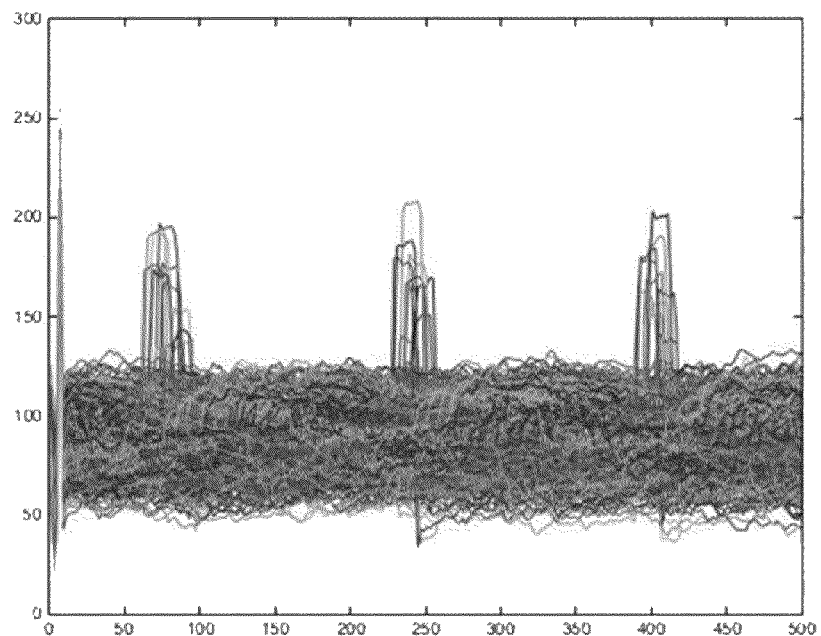
FIG. 3 shows a collection of approximately 1000 ERs obtained during a surgery, to depict the characteristics of a pacing pulse signal relative to the ER signals obtained by the system.
Figure 4:
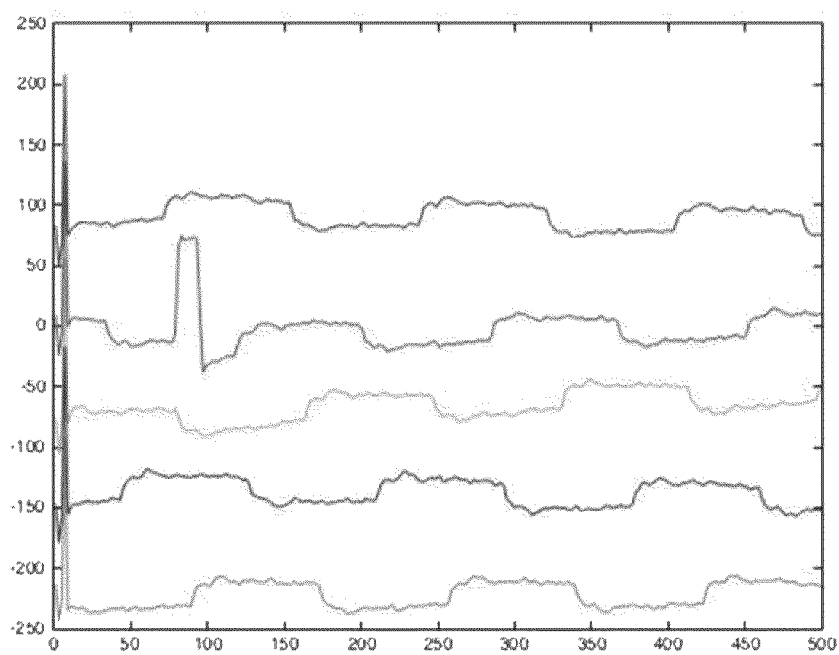
FIG. 4 shows five individual ERs, where one of the signals (second from top) is contaminated with a pacing artifact.

FIG. 3 shows a collection of approximately 1000 ERs obtained during a surgery, to depict the characteristics of a pacing pulse signal relative to the ER signals obtained by the system. FIG. 4 shows five individual ERs, where one of the signals (second from top) is contaminated with a pacing artifact. As shown in FIGS. 3 and 4, the pacing pulse has several characteristics that distinguish it from the ER signals. Accordingly, several key characteristics of the pacing artifact are focused upon in order to identify contaminated traces. Since the pacing artifact resembles a square wave, the characteristics identified as important are the magnitude of the rising and falling edges, the amplitude, and the level of activity in between the edges. The order in which the algorithm examines these features is decided by the degree of feature's definition. The most well-defined traits of the artifact are the distinctive rising and falling edges, therefore the algorithm may primarily look for a steep positive slope followed by a steep negative slope within some time range. The amplitude is then considered the next best defined trait, since the pacing artifact is significantly greater in magnitude than the rest of the data. Then, the level of activity between the two edges may be investigated.

Accordingly, in an exemplary embodiment of the present invention, the algorithm first looks for any ER that contain sudden increases in amplitude (signal having a steep rising edge), characteristic of non-physiological artifact. If none is present, no further processing is required. If this characteristic is present, the algorithm looks for the presence of a sudden decrease in amplitude occurring within a specified time or window length from initial increase. If this characteristic is present, the algorithm continues to analyze each ER through a series of characteristics which may include but are not limited to amplitude, rise time, peak duration and pre and post peak slope. If all defined characteristics are present it rejects the signal from the ensemble averaging. This process is described in greater detail below.

Since the artifact has a steep rising edge followed by a steep falling edge, the slopes of the original data are firstly taken into consideration. After taking the first difference of the pre-collected raw data, the algorithm would use a threshold trigger to start the identification process. Following an initial large positive slope, a pre-defined time window is set, starting at the point of threshold triggering, so that if there is a large negative slope within the window, the data has positively identified a first characteristic of a pacing signal (or similar noise), and the identification process moves on. If there is not a large negative slope within that time window, the algorithm ignores the original window starting point, and continues looking through that trace for a different positive slope.

If a large negative slope was confirmed within the time window, the amplitude of this deviation in the data is calculated. The amplitude is calculated by first recognizing a base for the data. The artifacts' onset and trough are not often the same voltage, and should be averaged to achieve a more consistent amplitude check. Once the base is established, the difference between the voltage of the base and the midpoint of the artifact is considered to be the amplitude. If the amplitude of the deviation is large enough, the algorithm continues the identification process, and if the amplitude of the deviation is smaller than the threshold value, then the process is stopped and the algorithm continues to look for the next large positive slope. This step is necessary to confirm that the deviation is large enough to be considered a pacing artifact, as there is often oscillatory noise in the raw data that contains relatively large positive and negative slopes in a small window.

Finally, the slope between the edges is examined to confirm if there is consistent data with little slope between the edges. The pacing artifact resembles a square wave, and therefore has little activity in between the two edges. If there is too much activity between the edges, this suggests that the deviation being analyzed is noise and not artifact. If the data between the two edges is "flat" enough, then the trace is identified as having an artifact, and the algorithm stops looking for a large positive slope. To be considered flat the data between the two edges has to have several data points with little to no slope.

In order to detect the characteristics described above to identify the traces with pacing artifact, threshold values for each piece of data is set. In some embodiments, the threshold values are set as shown in FIG. 5. A slope threshold (to identify a steep rising and falling edge) describes a minimum rate of change required to alert the algorithm to the possible existence of pacing artifact. In some embodiments, the slope minimum is 15. A window length describes the window of time in which the algorithm looks for the large positive and negative slope (i.e., the steep rising and falling edge). In some embodiments, the window length is 2.0 ms.

In other embodiments the window length may be between 2.0 to 2.5 ms. An amplitude threshold describes the minimum amplitude of the artifact, to confirm that processing to determine presence of a pacing artifact should continue on the current signal. In some embodiments, the amplitude minimum is 30 µV. Finally, the activity threshold describes the minimum number of data points to compare, to determine variability and slope between data points. In some embodiments, the minimum number of data points between the rising and falling edges, to determine activity, is three.

If the algorithm studies the entire trace as described above, and an artifact has not been identified, then the trace is identified as being "clean". The clean traces are then separated into one data set, while the "dirty" traces (those were a pacing artifact is identified) are separated into another. The clean data set can then be used to make an EA that would be void of pacing artifact. Since pacemaker artifact occurs out of phase with typical evoked potential stimuli and usually at a much slower rate, only a small subset of raw time recordings shows the artifact as present and exclusion of those from the ensemble average does not affect the overall integrity of the ensemble average (EA).

Figure 6B:
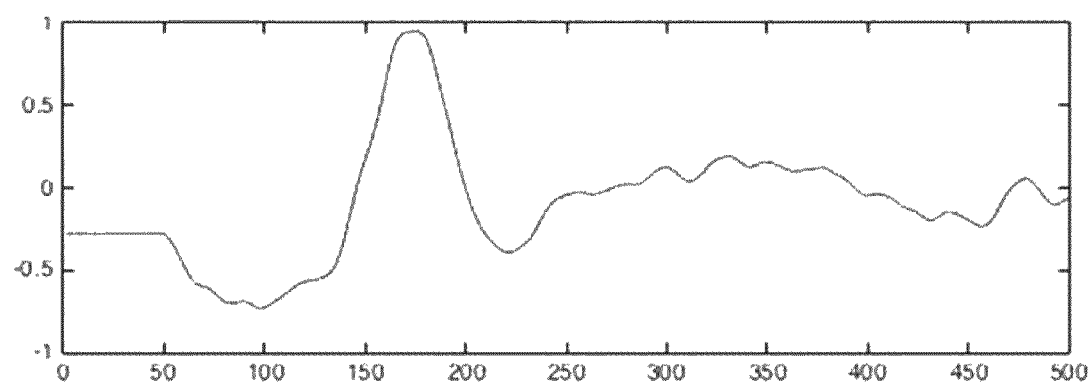
FIG. 6B depicts the somatosensory evoked potential recording of FIG. 6A, but with the signal recordings containing pacemaker artifact rejected before averaging.

FIGS. 6A and 6B provide a comparison showing the effect of the above-described methods on the obtained EA. FIG. 6A depicts an averaged somatosensory evoked potential recording contaminated by pacemaker artifact, while FIG. 6B depicts the somatosensory evoked potential recording of FIG. 6A, but with the signal recordings containing pacemaker artifact rejected before averaging. Accordingly, the EA of FIG. 6B provides a more accurate depiction of the signals being obtained by the system, in order to make a more accurate analysis of signals and determination of whether a nerve injury is impending.

Figure 7:
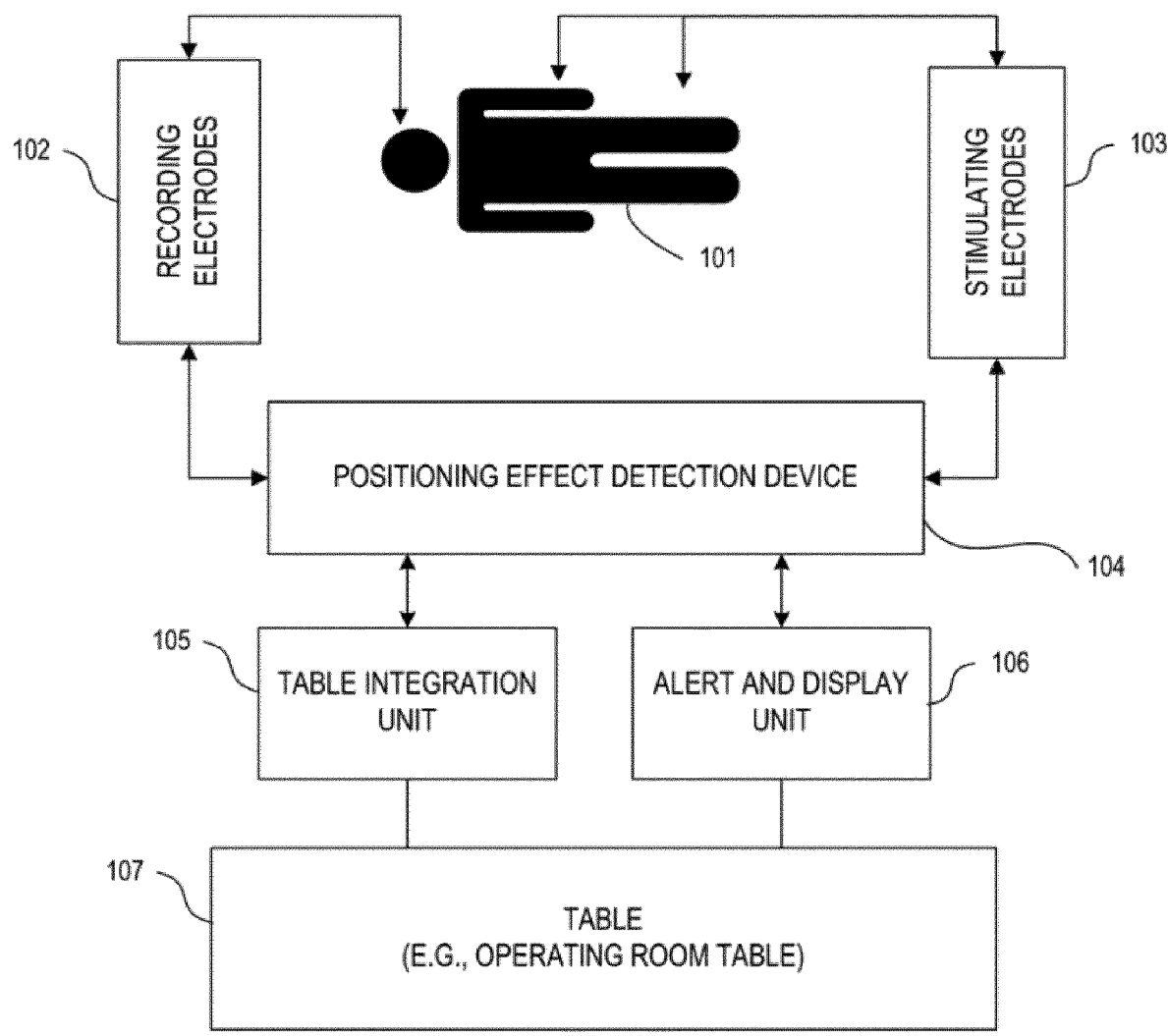
FIG. 7 depicts an exemplary diagram of the system according to an exemplary embodiment of the present invention.

FIG. 7 depicts an exemplary diagram of a system according to an exemplary embodiment of the present invention. According to an exemplary embodiment, the system 100, which may be coupled to a patient 101, may include, e.g., but not limited to, one or more recording electrodes 102, one or more stimulating electrodes 103, a positioning effect detection device (PEDD) 104, a table integration unit 105, an alert and display (or other output) unit 106, and a table 107. In an exemplary embodiment, the table 107 may include, e.g., but not limited to, any surface upon which the patient 101 may be placed, a bed, a chair, an operating room table, a pre-op table, and/or a post-op table, etc. Related or additional functions, components, capabilities, details, and other characteristics of such a system, not described herein, are described in U.S. Pat. No. 9,211,074, entitled "System, Method, Apparatus, Device, and Computer Program Product for Automatically Detecting Positioning Effect," which is hereby incorporated by reference in its entirety.

According to an exemplary embodiment, the recording electrodes 102 may be coupled to the head, neck, spine, arms, legs, trunk, Erb's point and/or torso of the patient 101, and stimulating electrodes 103 may be coupled to the arms and/or legs of the patient 101.

According to an exemplary embodiment, the PEDD 104 may be electronically coupled to recording electrodes 102 and stimulating electrodes 103. In an exemplary embodiment, the PEDD 104 may be part of, may be coupled to, and/or may include, a computer. According to an exemplary embodiment, the PEDD 104 may include a computer, such as, e.g., but not limited to, the computer set forth in and described further below with reference to FIG. 8. In an exemplary embodiment, PEDD 104 may be electrically, electronically, and/or mechanically coupled to the table integration unit 105 and/or the alert and display unit 106.

In an exemplary embodiment, the PEDD 104 may detect positioning effect in a patient 101 lying on the table 107 using the stimulating electrodes 103 and the recording electrodes 102. According to an exemplary embodiment, the PEDD 104 may communicate positioning effect information using the alert and display unit 106 to, e.g., operating room personnel.

According to an exemplary embodiment, the PEDD 104 may stimulate sensory or mixed nerves of the patient using the stimulating electrodes 103 to produce EPs. In an exemplary embodiment, a PEDD 104 may be attached, coupled and/or connected to the patient 101 with stimulating electrodes 103, e.g., near the arms or legs over peripheral nervous structures, such as, but not limited to, e.g., the ulnar nerves, median nerves and posterior tibial nerves.

According to an exemplary embodiment, the PEDD 104 may use the recording electrodes 102 to detect ERs generated by a patient's nervous system in response to the stimulation from the stimulating electrodes 103. These ERs may then be subject to the analysis described above to identify a pacing artifact and remove the signal containing the artifact from the averaged EPs.

According to an exemplary embodiment, based on the observed EPs, the PEDD 104 may identify potential positioning effect injuries caused by positioning of the patient 101. In an exemplary embodiment, the PEDD 104 may detect changes in the EPs, such as, e.g., but not limited to, changes in latency, changes in amplitude or changes in morphology. According to an exemplary embodiment, changes, such as, e.g., but not limited to, reductions or aberrations in the EPs may indicate a positioning effect. In an exemplary embodiment, the PEDD 104 may identify a particular nerve structure affected by positioning effect based on the EPs. The PEDD 104 may further recommend actions to ameliorate the positioning effect by recommending changes in position. In one exemplary embodiment, the PEDD 104 may move the patient automatically so as to prevent positioning effect injury to the patient 101.

Figure 8:
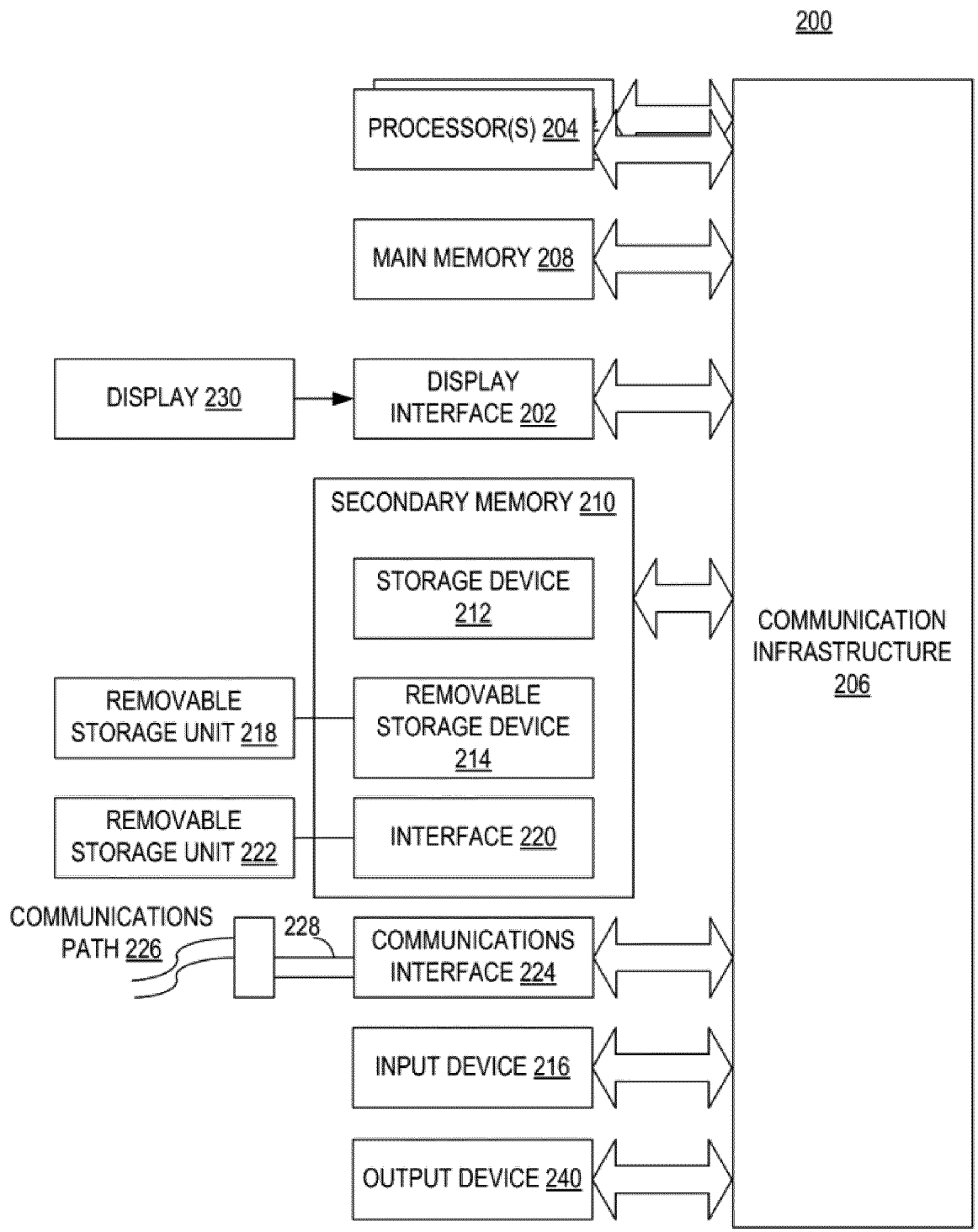
FIG. 8 depicts an exemplary embodiment of a computer system that may be used in association with an exemplary embodiment of the present invention.

FIG. 8 depicts an exemplary embodiment of a computer system 200 that may be used in association with, in connection with, and/or in place of, e.g., but not limited to, any of the foregoing components and/or systems.

The present embodiments (or any part(s) or function(s) thereof) may be implemented using hardware, software, firmware, or a combination thereof and may be implemented in one or more computer systems or other processing systems. In fact, in one exemplary embodiment, the invention may be directed toward one or more computer systems capable of carrying out the functionality described herein. An example of a computer system 200 is shown in FIG. 8, depicting an exemplary embodiment of a block diagram of an exemplary computer system useful for implementing the present invention. Specifically, FIG. 8 illustrates an example computer 200, which in an exemplary embodiment may be, e.g., (but not limited to) a personal computer (PC) system running an operating system such as, e.g., (but not limited to) WINDOWS MOBILE™ for POCKET PC, or MICROSOFT® WINDOWS® NT/98/2000/XP/CE/7/VISTA, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., Mac/OS from APPLE® Corporation of Cupertino, Calif., U.S.A., etc., or any of various versions of UNIX® (a trademark of the Open Group of San Francisco, Calif, USA) including, e.g., LINUX®, HPUX®, IBM AIX®, and SCO/UNIX®, etc. However, the invention may not be limited to these platforms. Instead, the invention may be implemented on any appropriate computer system running any appropriate operating system. In one exemplary embodiment, the present invention may be implemented on a computer system operating as discussed herein. An exemplary computer system, computer 200 is shown in FIG. 8. Other components of the invention, such as, e.g., (but not limited to) a computing device, a communications device, a telephone, a personal digital assistant (PDA), a personal computer (PC), a handheld PC, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 8.

The computer system 200 may include one or more processors, such as, e.g., but not limited to, processor(s) 204. The processor(s) 204 may be connected to a communication infrastructure 206 (e.g., but not limited to, a communications bus, cross-over bar, or network, etc.). Various exemplary software embodiments may be described in terms of this exemplary computer system. After reading this description, it will become apparent to a person skilled in the relevant art(s) how to implement the invention using other computer systems and/or architectures.

Computer system 200 may include a display interface 202 that may forward, e.g., but not limited to, graphics, text, and other data, etc., from the communication infrastructure 206 (or from a frame buffer, etc., not shown) for display on the display unit 230.

The computer system 200 may also include, e.g., but may not be limited to, a main memory 208, random access memory (RAM), and a secondary memory 210, etc. The secondary memory 210 may include, for example, (but may not be limited to) a hard disk drive 212 and/or a removable storage drive 214, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 214 may, e.g., but not limited to, read from and/or write to a removable storage unit 218 in a well-known manner. Removable storage unit 218, also called a program storage device or a computer program product, may represent, e.g., but not limited to, a floppy disk, a magnetic tape, an optical disk, a magneto-optical disk, a compact disk, a flash memory device, etc. which may be read from and written to by removable storage drive 214. As will be appreciated, the removable storage unit 218 may include a computer usable storage medium having stored therein computer software and/or data.

In alternative exemplary embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 222 and interfaces 220, which may allow software and data to be transferred from the removable storage unit 222 to computer system 200.

Computer 200 may also include an input device 216 such as, e.g., (but not limited to) a mouse or other pointing device such as a digitizer, and a keyboard or other data entry device (none of which are labeled).

Computer 200 may also include output devices 240, such as, e.g., (but not limited to) display 230, and display interface 202. Computer 200 may include input/output (I/O) devices such as, e.g., (but not limited to) communications interface 224, cable 228 and communications path 226, etc. These devices may include, e.g., but not limited to, a network interface card, and modems (neither are labeled). Communications interface 224 may allow software and data to be transferred between computer system 200 and external devices. Examples of communications interface 224 may include, e.g., but may not be limited to, a modem, a network interface (such as, e.g., an Ethernet card), a communications port, a Personal Computer Memory Card International Association (PCMCIA) slot and card, etc. Software and data transferred via communications interface 224 may be in the form of signals 228 which may be electronic, electromagnetic, optical or other signals capable of being received by communications interface 224. These signals 228 may be provided to communications interface 224 via, e.g., but not limited to, a communications path 226 (e.g., but not limited to, a channel). This channel 226 may carry signals 228, which may include, e.g., but not limited to, propagated signals, and may be implemented using, e.g., but not limited to, wire or cable, fiber optics, a telephone line, a cellular link, an radio frequency (RF) link and other communications channels, etc.

In this document, the terms "computer program medium" and "computer readable medium" may be used to generally refer to media such as, e.g., but not limited to removable storage drive 214, a hard disk installed in hard disk drive and/or other storage device 212, and signals 228, etc. These computer program products may provide software to computer system 200. The invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses and/or devices for performing the operations herein. An apparatus may be specially constructed for the desired purposes, or it may comprise a general purpose device selectively activated or reconfigured by a program stored in the device.

Embodiments of the invention may be implemented in one or a combination of hardware, firmware, and software. Embodiments of the invention may also be implemented as instructions stored on a machine-readable medium, which may be read and executed by a computing platform to perform the operations described herein. A machine-readable medium may include any mechanism for storing or transmitting information in a form readable by a machine (e.g., a computer). For example, an exemplary machine-readable storage medium may include, e.g., but not limited to, read only memory (ROM); random access memory (RAM); magnetic disk storage media; optical storage media; magneto-optical storage media; flash memory devices; other exemplary storage devices capable of storing electrical, optical, acoustical or other form of propagated signals (e.g., carrier waves, infrared signals, digital signals, etc.) thereon, and others.

Computer programs (also called computer control logic), may include object oriented computer programs, and may be stored in main memory 208 and/or the secondary memory 210 and/or removable storage units 214, also called computer program products. Such computer programs, when executed, may enable the computer system 200 to perform the features of the present invention as discussed herein. In particular, the computer programs, when executed, may enable the processor or processors 204 to provide a method to control and/or manage operation of a positioning effect detection device according to an exemplary embodiment of the present invention. Accordingly, such computer programs may represent controllers of the computer system 200.

In another exemplary embodiment, the invention may be directed to a computer program product comprising a computer readable medium having control logic (computer software) stored therein. The control logic, when executed by the processor 204, may cause the processor 204 to perform the functions of the invention as described herein. In another exemplary embodiment where the invention may be implemented using software, the software may be stored in a computer program product and loaded into computer system 200 using, e.g., but not limited to, removable storage drive 214, hard drive 212 or communications interface 224, etc. The control logic (software), when executed by the processor 204, may cause the processor 204 to perform the functions of the invention as described herein. The computer software may run as a standalone software application program running atop an operating system, or may be integrated into the operating system.

In yet another embodiment, the invention may be implemented primarily in hardware using, for example, but not limited to, hardware components such as application specific integrated circuits (ASICs), or one or more state machines, etc. Implementation of the hardware state machine so as to perform the functions described herein will be apparent to persons skilled in the relevant art(s).

In another exemplary embodiment, the invention may be implemented primarily in firmware. In yet another exemplary embodiment, the invention may be implemented using a combination of any of, e.g., but not limited to, hardware, firmware, and software, etc.

Exemplary embodiments of the invention may also be implemented as instructions stored on a machine-readable or accessible storage medium, which may be read and executed by a computing platform to perform the operations described herein. A machine-readable storage medium may include any mechanism for storing or transmitting information in a form readable by a machine (e.g., a computer). For example, a machine-readable medium may include, e.g., but not limited to, read only memory (ROM); random access memory (RAM); magnetic disk storage media; optical storage media; magneto-optical storage media; flash memory devices; other exemplary storage devices capable of storing electrical, optical, acoustical or other form of propagated signals (e.g., carrier waves, infrared signals, digital signals, etc.) thereon, and others.

The exemplary embodiment of the present invention makes reference to, e.g., but not limited to, communications links, wired, and/or wireless networks. Wired networks may include any of a wide variety of well-known means for coupling voice and data communications devices together. Alternatively, various exemplary wireless network technologies may be used to implement the embodiments of the present invention.

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

According to an exemplary embodiment, exemplary methods set forth herein may be performed by an exemplary one or more computer processor(s) adapted to process program logic, which may be embodied on an exemplary computer accessible storage medium, which when such program logic is executed on the exemplary one or more processor(s) may perform such exemplary steps as set forth in the exemplary methods.

What is claimed is:

1. An apparatus for automated analysis of evoked potentials, the apparatus comprising:
    an output coupled to at least one stimulating electrode to stimulate at least one peripheral nerve of a patient;
    an input coupled to at least one recording electrode to record an electrophysiological response comprising a plurality of resultant electrical waveforms generated by a nervous system of the patient in response to the stimulation from the at least one stimulating electrode; and
    at least one processor coupled to the output and the input, the at least one processor programmed to execute an automated evoked potential analysis algorithm for monitoring, detecting, identifying and eliminating non-physiological artifact noise in the physiological system from which the evoked potentials or ensemble averages of the evoked potentials are obtained, the automated evoked potential analysis algorithm configured to:
- determine whether ambient electrical noise or non-physiological artifact noise is present in a resultant electrical waveform of the plurality of electrical waveforms of the electrophysiological response;
- detecting, based on the determination, that the non-physiological artifact noise is present in the resultant electrical waveform, the detecting comprising:
- identifying in the electrophysiological response, at least one characteristic representative of a signal having the non-physiological artifact noise;
  - classify the resultant electrical waveform as an artifact signal if the non-physiological artifact noise is present;
  - remove the resultant electrical waveform that has been identified as the artifact signal from a collection of signals;
  - generate an averaged evoked potential signal from the collection of signals; and
- generate positioning effect information about the patient using the averaged evoked potential signal.

2. The apparatus of claim 1, wherein the non-physiological artifact noise is pacing artifact from a pacemaker.

3. The apparatus of claim 1, wherein the at least one characteristic is at least one from the group consisting of: a minimum slope, a minimum amplitude, a maximum rise time, a maximum fall time, a minimum peak duration, and a maximum activity between a rising edge and a falling edge of the signal.

4. The apparatus of claim 1, wherein the at least one processor is further configured to transmit the positioning effect information to display or generate an alert based on the positioning effect information.

5. The apparatus of claim 1, wherein the at least one stimulating electrode is coupled to arms and/or legs of the patient.

6. The apparatus of claim 1, wherein the at least one recording electrode is coupled to a head, neck, spine, arms, legs, trunk, Erb's point and/or torso of the patient.

7. The apparatus of claim 1, wherein the collection of signals used to generate an averaged evoked potential signal comprises the remaining resultant electrical waveforms of the plurality of electrical waveforms in which the non-physiological artifact noise is not present.

* * * * *